United States Patent
Kanazawa et al.

(10) Patent No.: US 10,493,234 B2
(45) Date of Patent: Dec. 3, 2019

(54) CATHETER

(71) Applicant: ASAHI INTECC CO., LTD., Seto-shi, Aichi (JP)

(72) Inventors: Yuya Kanazawa, Seto (JP); Keisuke Ushida, Nagoya (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 0 days.

(21) Appl. No.: 15/072,854

(22) Filed: Mar. 17, 2016

(65) Prior Publication Data

US 2016/0279383 A1    Sep. 29, 2016

(30) Foreign Application Priority Data

Mar. 23, 2015 (JP) .................... 2015-059997
Mar. 23, 2015 (JP) .................... 2015-059998
Dec. 11, 2015 (JP) .................... 2015-242279

(51) Int. Cl.
  *A61M 25/00* (2006.01)
  *A61M 25/09* (2006.01)

(52) U.S. Cl.
  CPC ........ *A61M 25/005* (2013.01); *A61M 25/001* (2013.01); *A61M 25/0012* (2013.01);
  (Continued)

(58) Field of Classification Search
  CPC ................ A61M 25/00; A61M 25/001; A61M 25/0068; A61M 25/005; A61M 25/0012;
  (Continued)

(56) References Cited

U.S. PATENT DOCUMENTS 4,682,607 A * 7/1987 Vaillancourt ......... A61M 25/09
                                                        600/434
6,258,195 B1 * 7/2001 Holman ............ A61M 25/0012
                                                        156/166
(Continued)

FOREIGN PATENT DOCUMENTS

EP      2845620 A1      3/2015
EP    2 937 108 A1    10/2015
(Continued)

OTHER PUBLICATIONS

Aug. 22, 2016 Search Report issued in European Patent Application No. 16157125.2.
(Continued)

*Primary Examiner* — Imani N Hayman
*Assistant Examiner* — Tiffany Legette
(74) *Attorney, Agent, or Firm* — Oliff PLC

(57) ABSTRACT

A catheter has excellent torque transmissivity and excellent flexibility, thus enabling easy insertion of the catheter into a blocked portion of a blood vessel. Additionally, the catheter easily restores to its original form even when the catheter is curved and deformed a large amount. Thus, a break at a border area between a catheter main body part and a distal end tip is prevented when the catheter is bent and deformed. This improves the operability of the catheter with a combination device such as a guide wire. The catheter includes a hollow coil body formed of at least one helically wound stranded wire. The at least stranded wire includes a plurality of wires wound into a helical structure.

12 Claims, 15 Drawing Sheets

(52) U.S. Cl.
CPC ............ *A61M 25/0068* (2013.01); *A61M 2025/09066* (2013.01); *A61M 2025/09175* (2013.01); *A61M 2025/09191* (2013.01)

(58) Field of Classification Search
CPC ......... A61M 2025/09191; A61M 2025/09175; A61M 2025/09066
USPC ........................................................ 604/526
See application file for complete search history.

(56) References Cited

U.S. PATENT DOCUMENTS

| | | | |
|---|---|---|---|
| 2005/0222585 A1 | 10/2005 | Miyata et al. | |
| 2006/0178653 A1 | 8/2006 | Shimogami et al. | |
| 2007/0088230 A1 | 4/2007 | Terashi et al. | |
| 2008/0255518 A1* | 10/2008 | Albers | A61M 25/09 600/585 |
| 2010/0094258 A1* | 4/2010 | Shimogami | A61M 25/005 604/527 |
| 2014/0214006 A1* | 7/2014 | Hiroshige | A61M 25/0012 604/527 |
| 2014/0276074 A1 | 9/2014 | Warner | |
| 2016/0151078 A1 | 6/2016 | Kanazawa | |

FOREIGN PATENT DOCUMENTS

| | | |
|---|---|---|
| JP | H06-511162 A | 12/1994 |
| JP | 2005-296078 A | 10/2005 |
| JP | 2006-174959 A | 7/2006 |
| JP | 2006-519072 A | 8/2006 |
| JP | 2007-098120 A | 4/2007 |
| JP | 2008-155052 A | 7/2008 |
| JP | 2011-110144 A | 6/2011 |
| JP | 2014-100265 A | 6/2014 |
| JP | 2014-144163 A | 8/2014 |
| JP | 2014-236863 A | 12/2014 |
| JP | 2015-13005 A | 1/2015 |
| JP | 2015-051085 A | 3/2015 |
| WO | 1992/19308 A1 | 11/1992 |
| WO | 2004/075968 A1 | 9/2004 |

OTHER PUBLICATIONS

Apr. 24, 2018 Office Action issued in Japanese Patent Application No. 2015-242279.

Nov. 6, 2018 Office Action issued in Japanese Patent Application No. 2015-242279.

May 21, 2019 Office Action issued in Japanese Patent Application No. 2015-242279.

* cited by examiner

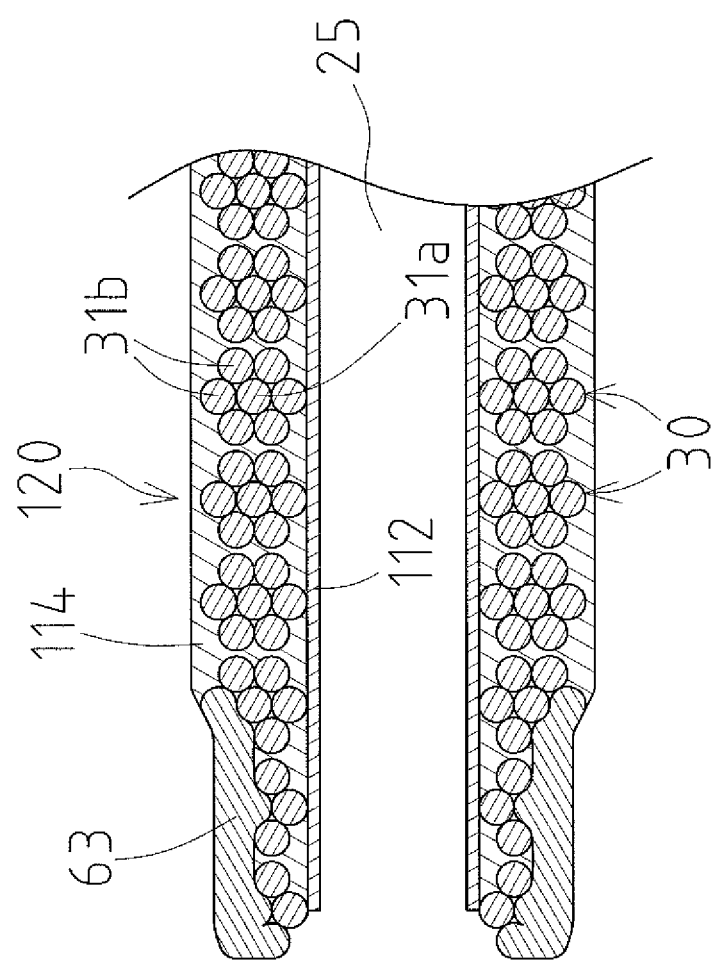

CATHETER

CROSS REFERENCE TO RELATED APPLICATION

This application claims priority to Japanese Patent Application No. 2015-242279, filed in the Japan Patent Office on Dec. 11, 2015, Japanese Patent Application No. 2015-059998, filed in the Japan Patent Office on Mar. 23, 2015, and Japanese Patent Application No. 2015-059997, filed in the Japan Patent Office on Mar. 23, 2015, the entire contents of which are incorporated by reference.

BACKGROUND

The disclosed embodiments relate to a catheter for medical use.

Conventional balloon catheters include a catheter main body, formed by winding a wire into a helical coil structure, and a distal end tip that is fixed to a distal end of the catheter main body.

For example, Patent Literature 1 (identified below) discloses a medical treatment instrument (catheter) in which a metal distal end tip is attached to a distal end of a coil body, which is formed by winding metal wires.

Patent Literature

Patent Literature 1: Japanese Patent Application Laid-open No. 2007-98120

SUMMARY

However, in the above-described conventional catheters, including the catheter of Patent Literature 1, the coil body is formed by winding a single piece of wire into a single line (single line coil body) or a plurality of wires into a multi-line (multi-line coil body). In a single line coil body, torque transmissivity of the coil body is reduced. In a multi-line coil body, flexibility of the coil body is reduced. Therefore, it is difficult to easily insert a conventional catheter into, for example, a blocked portion of a blood vessel.

Furthermore, the catheter of Patent Literature 1 may be slightly deformed when its degree of curvature becomes large. Once the catheter is deformed, its original form cannot be restored. Thus, in such a case, the operation of the catheter with a combination device, such as a guide wire, may become difficult.

The catheter of Patent Literature 1 also has a metal distal end tip that is separately connected to a distal end of the catheter main body. Thus, stress is concentrated at a border part between the catheter main body and the distal end tip, which may cause a break at such a border part. For example, a break may occur at such a border part when the catheter is bent.

The metal distal end tip of the catheter of Patent Literature 1 is separately connected to the distal end of the catheter main body. Thus, a combination device, such as a guide wire, may be caught at the border part between the catheter main body and the distal end tip, increasing resistance when the combination device is pushed or pulled.

The coil body of the catheter of Patent Literature 1 is formed by winding a single piece of wire into a single line (single line coil body) or a plurality of wires into a multi-line (multi-line coil body), and the wire forming the coil body is inclined relative to a long axis direction of the catheter. This increases insertion resistance when the catheter is inserted into, for example, a blocked portion of a blood vessel.

The present disclosure provides a catheter with excellent torque transmissivity and excellent flexibility, allowing easy insertion of the catheter into a blocked portion of a blood vessel or the like.

The present disclosure also provides a catheter that is capable of easily restoring its original form even when the degree of curvature of the catheter becomes large and the catheter is deformed.

The present disclosure also provides a catheter that is capable of preventing a break at a border part between a catheter main body and a distal end tip, thus improving the operability of the catheter with a combination device, such as a guide wire.

The disclosed embodiments include a catheter including a coil body wound into a hollow helical coil structure by a stranded wire. The stranded wire being formed of a plurality of wires.

The disclosed embodiments include a hollow coil body that is formed of at least one helically wound stranded wire. The stranded wire includes a plurality of stranded wires wound into a helical structure.

BRIEF DESCRIPTION OF THE DRAWINGS

FIG. 15 is a partial section view illustrating a distal end portion of a catheter according to the disclosed embodiments.

DETAILED DESCRIPTION OF EMBODIMENTS

In the following description, embodiments of the present disclosure will be described with reference to the enclosed drawings.

Figure 1:
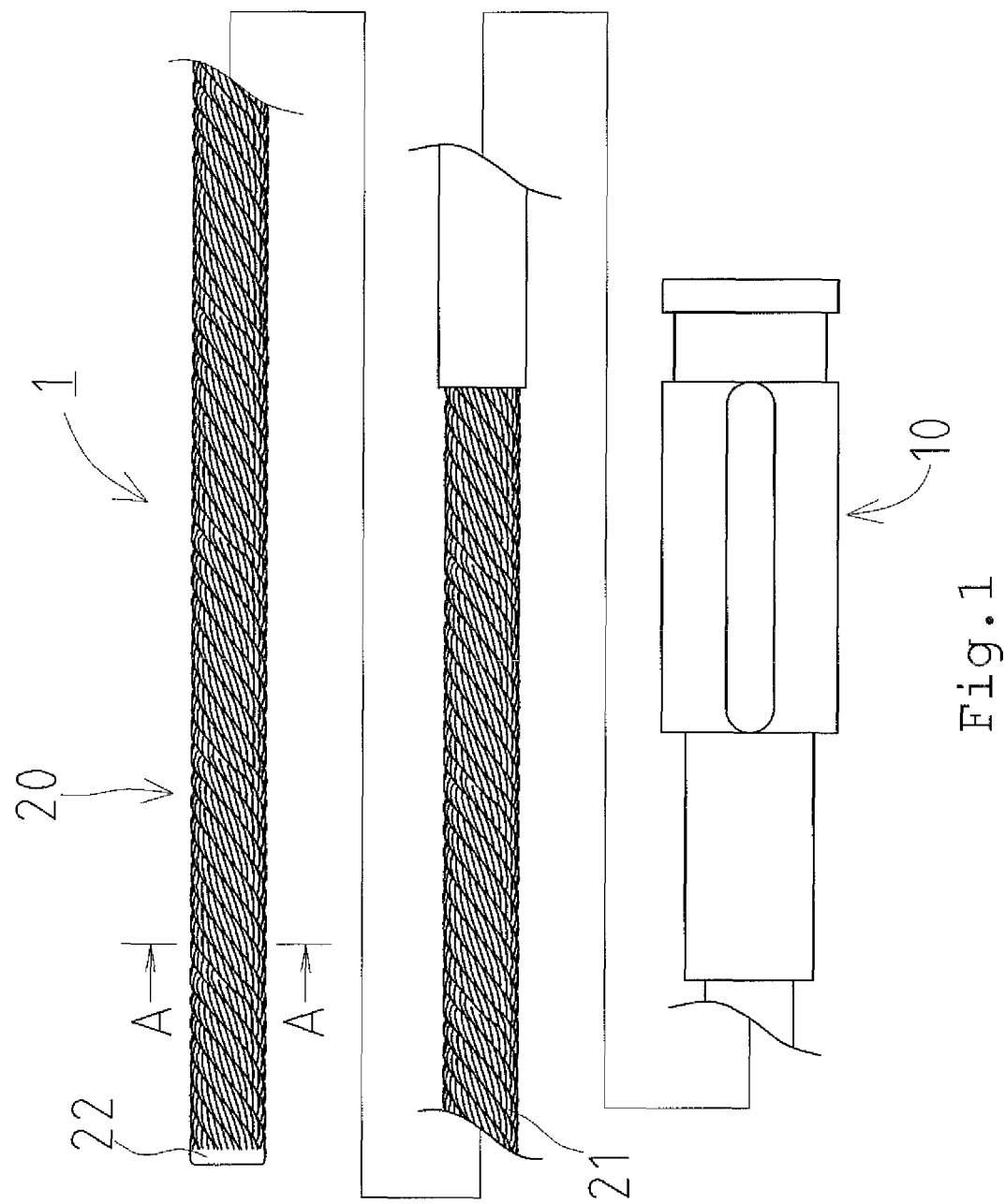
FIG. 1 is a plan view of a catheter according to the disclosed embodiments.
Figure 2:
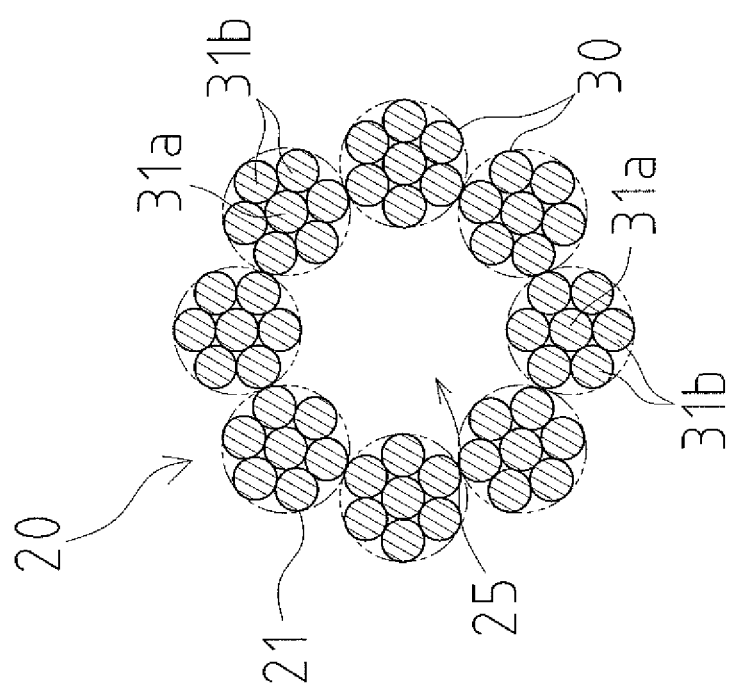
FIG. 2 is a section view taken from a line A-A of FIG. 1.
Figure 3:
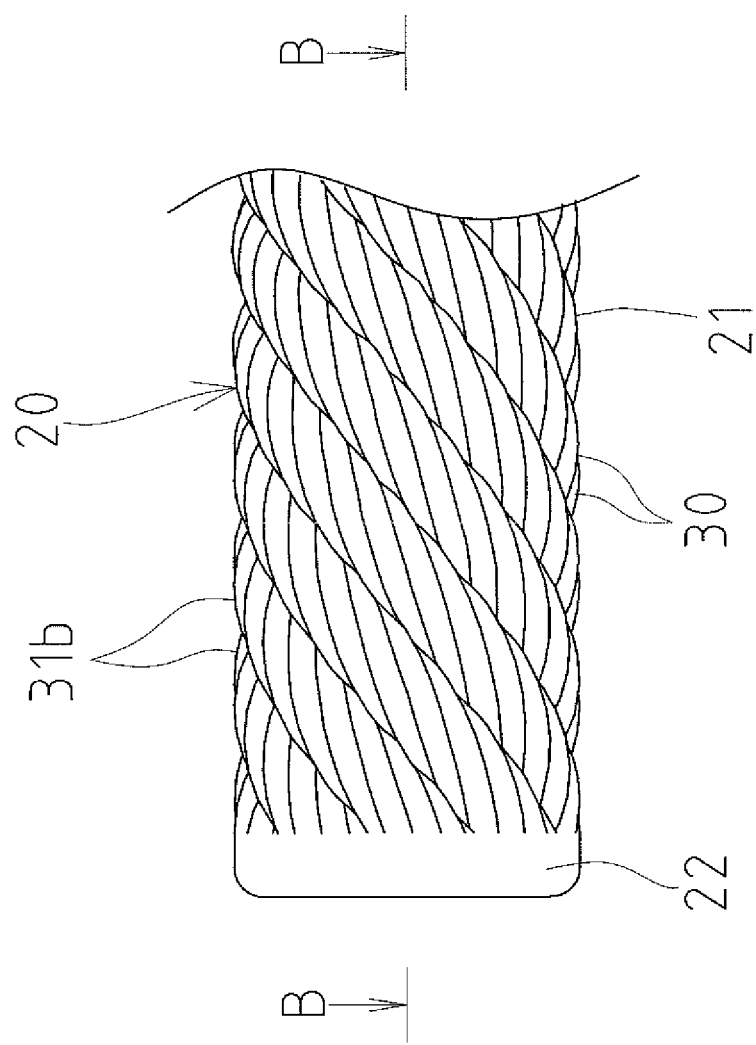
FIG. 3 is a partial enlarged view illustrating a distal end portion of the catheter of FIG. 1.
Figure 4:
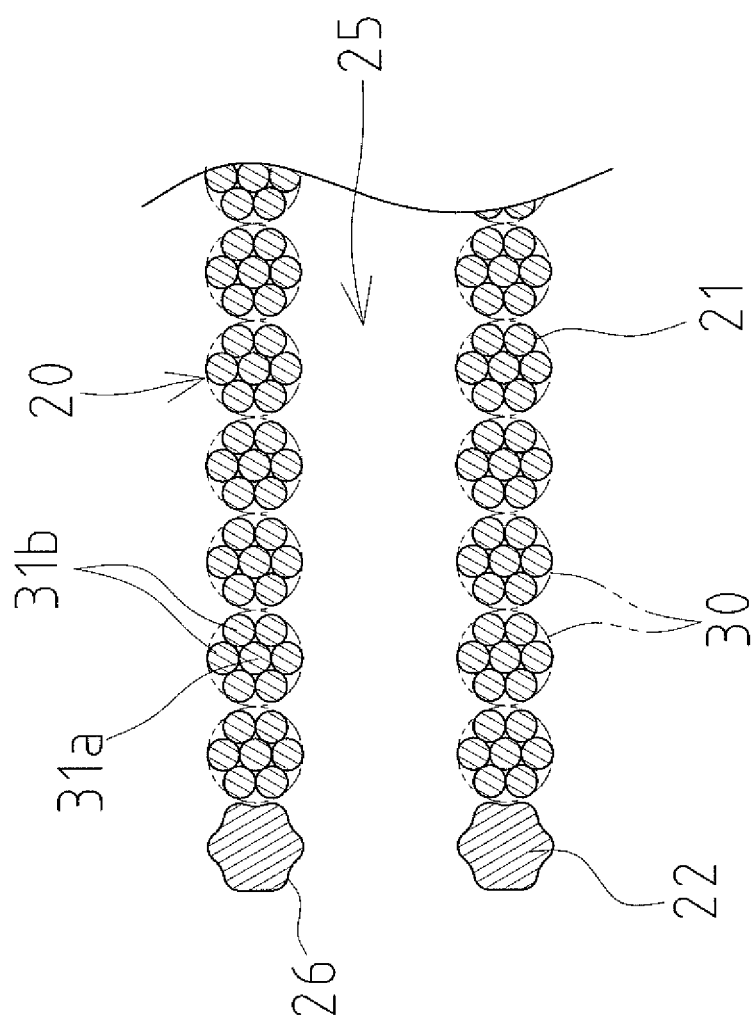
FIG. 4 is a partial section view taken from a line B-B of FIG. 3.

FIG. 1 is a plan view of a catheter according to embodiments of the present disclosure. FIG. 2 is a section view taken from a line A-A of FIG. 1. FIG. 3 is a partial enlarged view illustrating a distal end portion of the catheter of FIG. 1. FIG. 4 is a partial section view taken from a line B-B of FIG. 3.

As illustrated in FIG. 1, catheter 1 includes an operation part 10 that is operated by a technician and a coil body 20 that is connected to a distal end of the operation part 10.

Moreover, the coil body 20 includes a main body part 21 that extends from the operation part 10 toward a distal end side of the catheter 1 and a distal end portion 22 that is positioned distally of the main body part 21. Additionally, the coil body 20 includes a hollow part 25 (see FIG. 2) that is formed in the main body part 21 and in the distal end portion 22.

As illustrated in FIG. 2, the main body part 21 of the coil body 20 is tubular and includes, for example, eight bundles of stranded wire 30 that are wound into a multi-line coil form. The stranded wire 30 may be formed, for example, by twisting six pieces of stainless steel second wire 31b (as side wire) around stainless steel first wire 31a (as a core wire). However, it is contemplated that alternative numbers of stranded wire 30, first wire 31a, and second wire 31b may be used.

Furthermore, as illustrated in FIG. 3 and FIG. 4, the distal end portion 22 of the coil body 20 is formed so that the distal ends of the stranded wire 30, positioned at the distal end portion 22, are fused and bonded together by, for example, YAG welding to prevent the first wire(s) 31a and the second wire(s) 31b from coming undone. The distal end portion 22 also includes a distal end opening portion 26 that is in communication with the hollow part 25.

The coil body 20 may be formed, for example, by winding a plurality of stranded wires 30 into a helical coil structure. Thus, torque transmissivity of the catheter 1 is improved without impairing flexibility of the catheter 1. Accordingly, insertion of the catheter 1 into a blocked portion of a blood vessel, or the like, is improved. For example, the catheter 1 easily restores to its original form when, during use, the catheter 1 is bent and curved a large amount.

As illustrated in FIG. 1 and FIG. 3, on an inner peripheral surface side and an outer peripheral surface side of the coil body 20, a twisting direction of the second wires 31b forming the stranded wire 30 is substantially parallel to a long axis direction of the catheter 1 (the longitudinal axis). This improves insertion of the catheter 1 into a blocked portion of a blood vessel, and improves operability of the catheter 1 with a combination device such as a guide wire.

In some embodiments, stainless steel is used as a material of the first wire 31a and the second wire 31b. However, other metal wires such as a superelastic alloy, such as an Ni—Ti alloy, a tungsten wire, or the like, may be used. Furthermore, the first wire 31a may be formed of the same or a different material from the second wire 31b.

In one embodiment, the number of wires forming the stranded wire 30 is seven. However, the number of first wires 31a and second wires 31b is not especially limited as long as it is two or more. From the viewpoint of torque transmissivity, flexibility, and the like, the number is preferably in the range of three to ten.

The coil body 20 may be formed by winding one bundle of stranded wire 30. However, in some embodiments, the coil body may be formed by winding a plurality of bundles of stranded wire 30. When the coil body 20 is formed by winding a plurality of bundles of stranded wire 30, insertion of the catheter 1 into a blocked portion of a blood vessel is further improved. Additionally, operability of the catheter 1 with a combination device such as a guide wire is also improved, and the catheter 1 is able to restore its original form more easily.

The distal end portion 22 may be formed by fusing the first wire(s) 31a and the second wire(s) 31b together. However, the main body part 21 may be formed of a plurality of stranded wires 30, and the distal end portion 22 may be provided separately from the main body part 21. In such a case, the catheter 1 has excellent torque transmissivity and excellent flexibility, improving insertion of the catheter 1 into a blocked portion of a blood vessel and allowing the catheter 1 to easily restore to its original form after being curved.

When the distal end portion 22 is formed by fusing the first wire(s) 31a and the second wire(s) 31b together, it is possible to further improve insertion of the catheter 1 into a blocked portion of a blood vessel, the operability of the catheter 1 with a combination device such as a guide wire, and the shape restorability of the catheter 1.

The distal end portion 22 may be fused by welding the first wire(s) 31a and the second wire(s) 31b together. However, the distal end portion 22 may be formed by a method other than welding. For example, the distal end portion 22 may be formed by brazing the first wire(s) 31a and the second wire(s) 31b.

Figure 5:
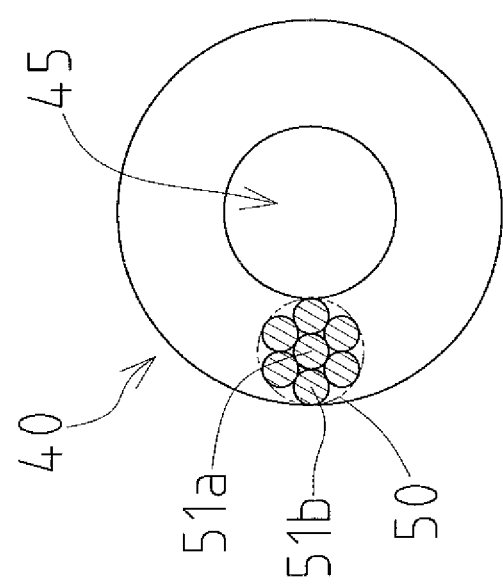
FIG. 5 is a section view of a catheter according to the disclosed embodiments.
Figure 6:
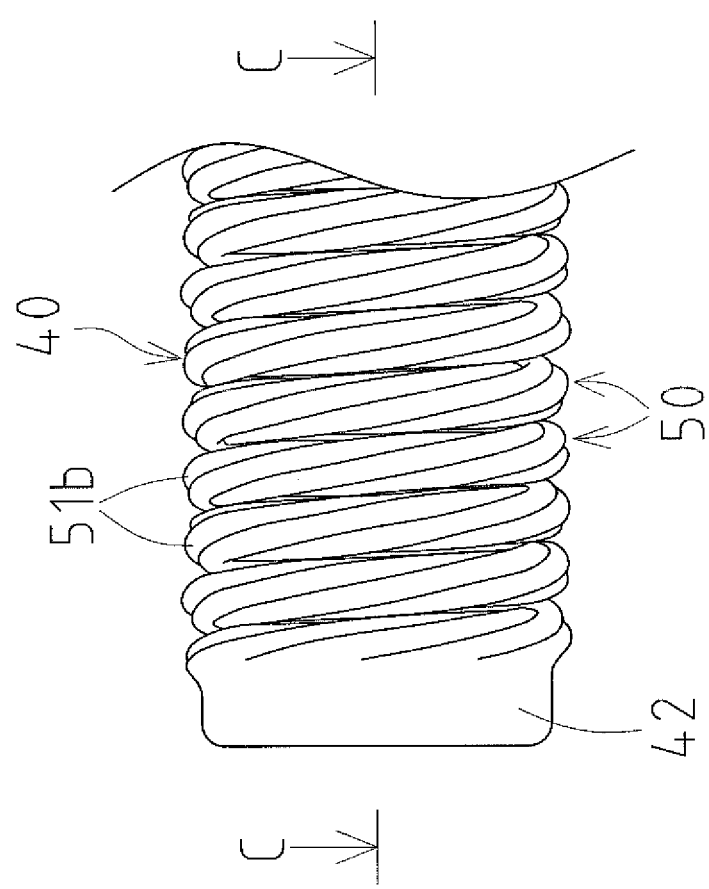
FIG. 6 is a partial enlarged view illustrating a distal end portion of the catheter of FIG. 5.
Figure 7:
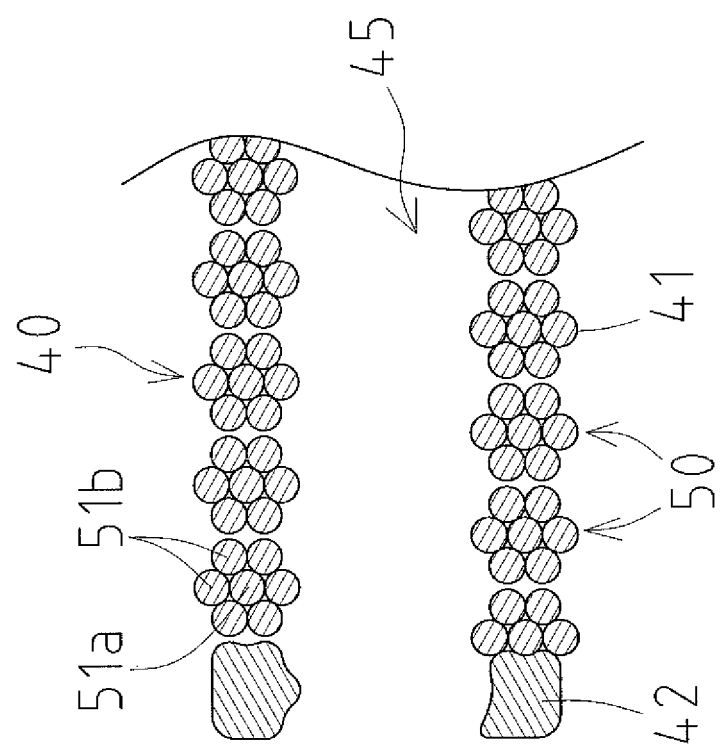
FIG. 7 is a partial section view taken from a line C-C of FIG. 6.

FIG. 5 is a section view of a catheter according to embodiments of the present disclosure. FIG. 6 is a partial enlarged view illustrating a distal end portion of the catheter of FIG. 5. FIG. 7 is a partial section view taken from a line C-C of FIG. 6.

The catheter of FIG. 5 is similar to the catheter 1 except that the catheter of FIG. 5 includes a different number of stranded wires 30. In some embodiments, the main body part 21 of the coil body 20 of the catheter 1 is wound by eight bundles of stranded wire 30 in a multi-line coil form (see FIG. 2). However, a main body part 41 of a coil body 40, as shown in FIGS. 5 and 6, is wound by one bundle of stranded wire 30 into a single line coil form. Thus, a single stranded wire 30 is wound to form the coil body 40.

In FIG. 5, the catheter may be formed by twisting six pieces of stainless steel second wire 51b (as side wire) around stainless steel first wire 51a (as a core wire). However, alternative numbers of first wire 51a and second wire 51 may be used. Similar to the catheter 1, the coil body 40 includes the main body part 41, which extends from the operation part 10 toward the distal end side of the catheter, and a distal end portion 42, which is positioned distally of the main body part 41. Additionally, a hollow part 45 is formed in the main body part 41 and in the distal end portion 42. As shown in FIG. 7, the distal end portion 42 of the coil body 40 is formed so that the distal ends of the stranded wire 50, positioned at the distal end portion 22, are fused and bonded together by, for example, YAG welding to prevent the first wire(s) 51a and the second wire(s) 51b from coming undone.

The coil body 40 is formed by winding one bundle of stranded wire 50 into a hollow helical coil structure. Thus, flexibility of the catheter is further improved, and catheter is able to be easily restored to its original position after being curved and bent.

As illustrated in FIG. 6, a twisting direction of the second wires 51b is substantially vertical relative to a long axis direction of the catheter (the longitudinal axis).

Figure 8:
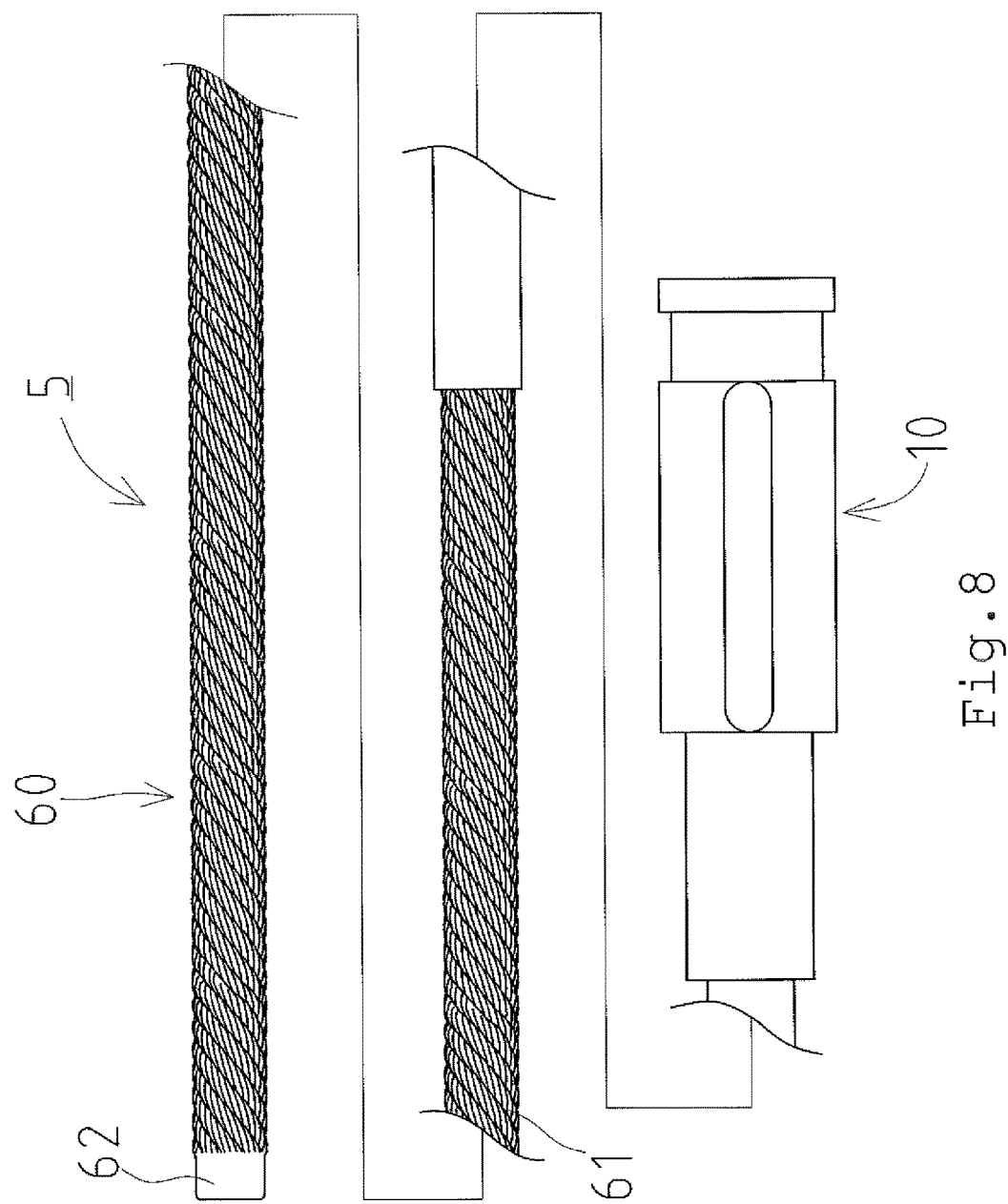
FIG. 8 is a plan view of a catheter according to the disclosed embodiments.
Figure 9:
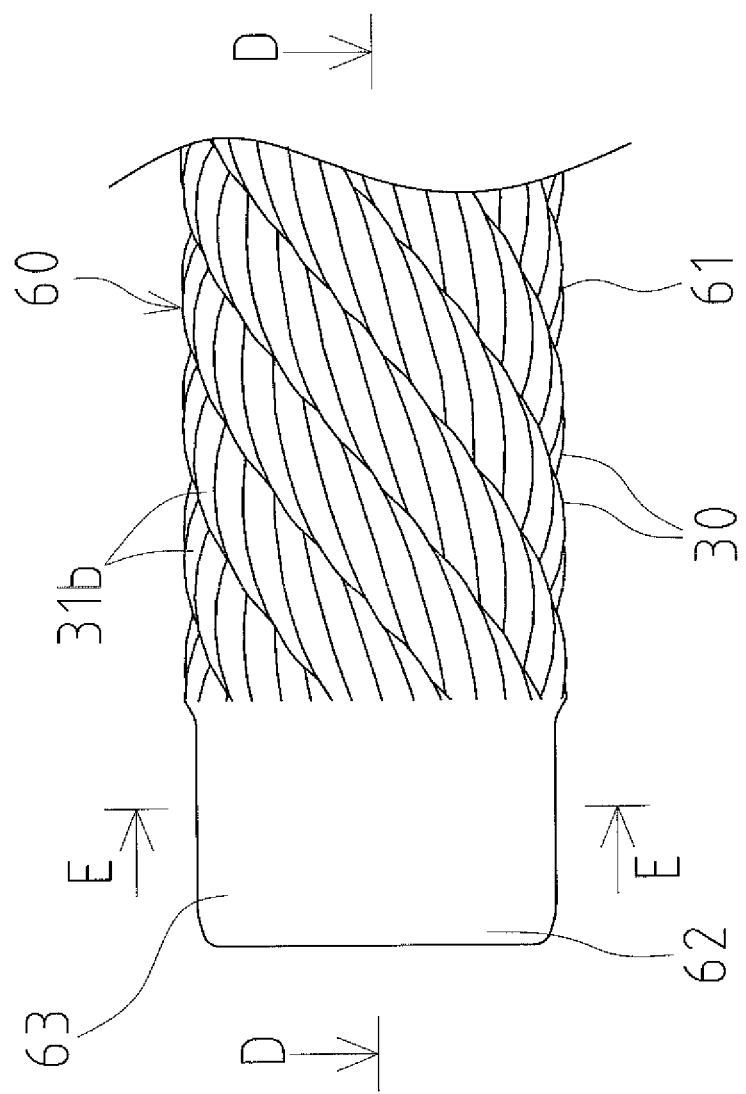
FIG. 9 is a partial enlarged view illustrating a distal end portion of the catheter of FIG. 8.
Figure 10:
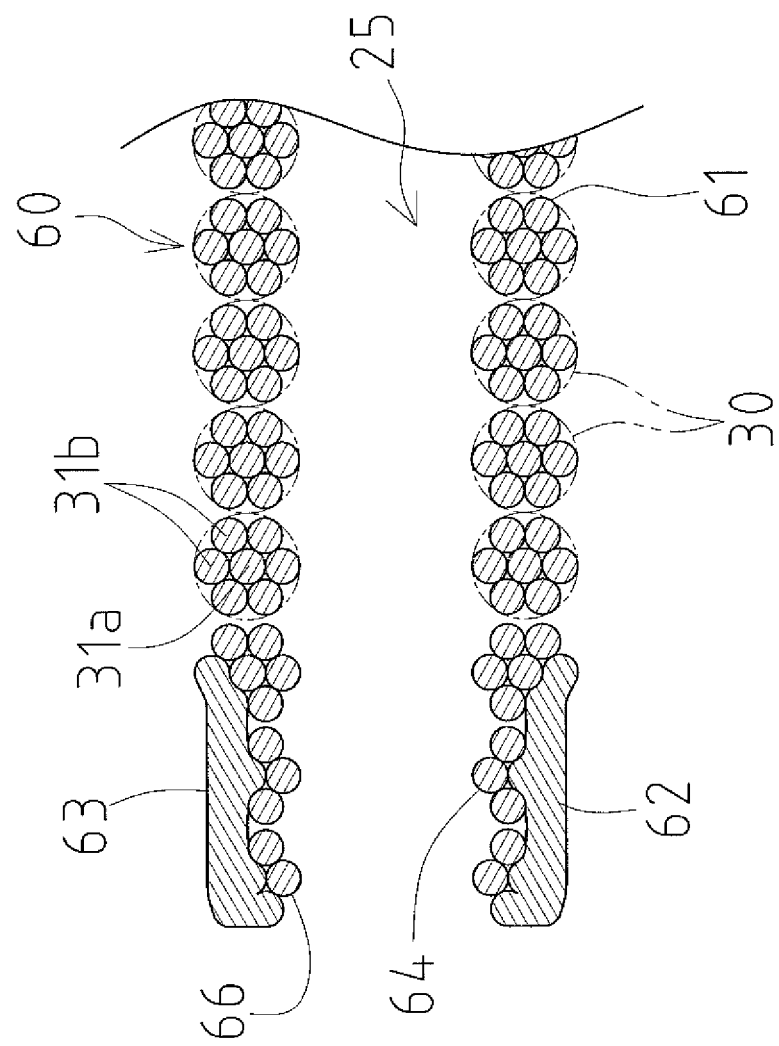
FIG. 10 is a partial section view taken from a line D-D of FIG. 9.
Figure 11:
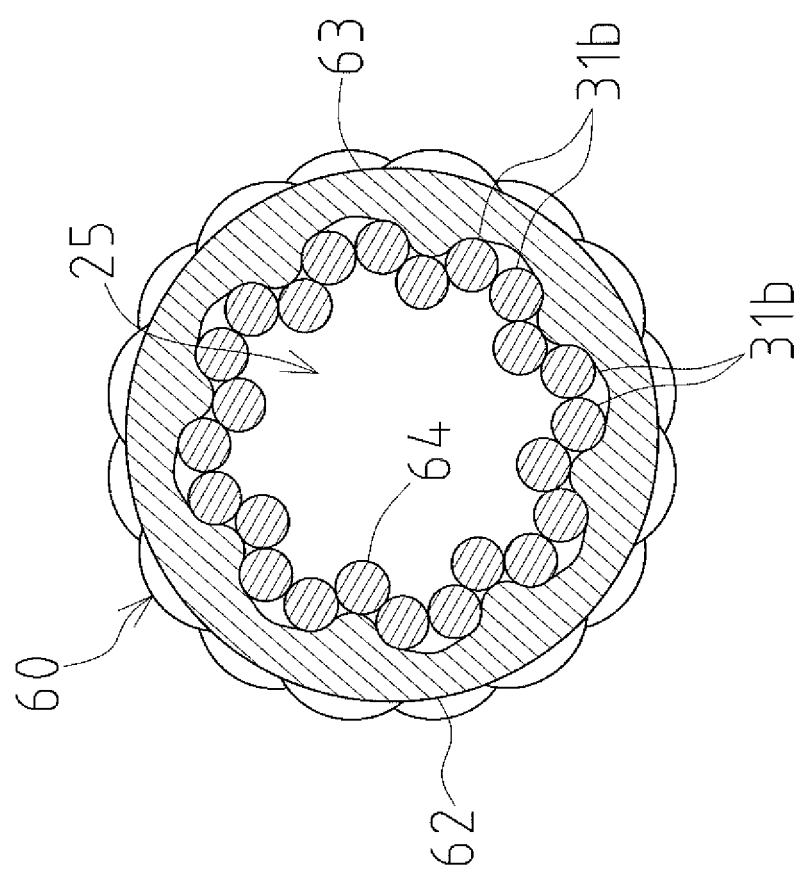
FIG. 11 is an end face view taken from a line E-E of FIG. 9.

FIG. 8 is a plan view of a catheter 5 according to disclosed embodiments. FIG. 9 is a partial enlarged view illustrating a distal end portion of the catheter 5 of FIG. 8. FIG. 10 is a partial section view taken from a line D-D of FIG. 9. FIG. 11 is an end face view taken from a line E-E of FIG. 9.

The catheter 5 is similar to the catheter 1 except regarding the fusion of the first wire(s) 31a and the second wire(s) 31b. The distal end portion 22 of the coil body 20 of the catheter 1 is formed by fusing distal ends of the entire width (entirety) of the first wire(s) 31a and the second wire(s) 31b. However, as shown in FIGS. 8-10, in a distal end portion 62 of a coil body 60 of the catheter 5, the second wire(s) 31b is not fused on an inner peripheral surface 64 of the distal end portion 62. Instead, the outer profile of the stranded wire 30 is maintained on the inner peripheral surface 64. Thus, the inner peripheral surface 64 is uneven due to the outer profile of the second wire 31b.

Similar to the catheter 1, the coil body 60 includes a main body part 61 that extends from the operation part 10 toward the distal end side of the catheter 5. The distal end portion 62 is positioned distally of the main body part 61, and the hollow part 25 is formed in the main body part 61 and in the distal end portion 62. Furthermore, the main body part 61 of the coil body 60 may be wound, for example, by eight bundles of stranded wire 30 in a multi-line coil similar to the catheter 1, as shown in FIG. 4.

As shown in FIGS. 9-11, on an outer peripheral surface 63 at the distal end portion 62, the first wire(s) 31a and the second wire(s) 31b are fused and bonded together by, for example, YAG welding to prevent the first wire(s) 31a and the second wire(s) 31b from coming undone. Thus, the outer peripheral surface 63 at the distal end portion 62 is a smooth surface.

FIG. 11 illustrates that the first wire(s) 31a and the second wire(s) 31b positioned on the outer peripheral surface 63 are fused together. However, a part of the first wire(s) 31a and a part of the second wire(s) 31b (portions on the inner peripheral surface 64) are not fused together.

By welding, it is possible to easily fuse only the first wire(s) 31a and the second wire(s) 31b corresponding to the outer peripheral surface 63 without fusing the first wire(s) 31a and the second wire(s) 31b corresponding to the inner peripheral surface 64.

A distal end opening portion 66 at the distal end of the distal end portion 62 is in communication with the hollow part 25 and, as illustrated in FIG. 10, the stranded wire 30 positioned at the distal end of the distal end portion 62 is fused so as not to come undone.

In the coil body 60, the outer peripheral surface 63 of the distal end portion 62 is a smooth surface. Thus, resistance from when the catheter 5 is inserted into a blocked portion of a blood vessel, for example, is reduced, thereby improving insertion of the catheter 5 into the blocked portion. The inner peripheral surface 64 of the distal end portion 62 is uneven because it maintains the outer profile of the stranded wire 30. Thus, resistance between a combination device (e.g., guide wire) that is inserted into the hollow part 25 and the inner peripheral surface 64 is reduced by reducing the contact area between the combination device and the inner peripheral surface 64, thereby suppressing sliding resistance and improving operability.

A twisting direction of the second wire 31b is substantially parallel to a long axis direction of the catheter (the longitudinal axis). Thus, it is possible to further improve the operability of the catheter 5 with a combination device such as a guide wire.

Moreover, the distal end portion 62 and the main body part 61 may be integral such that they are formed as a unitary member. This prevents concentration of stress that would cause a break at a border area between the distal end portion 62 and the main body part 61.

Furthermore, the coil body 60 is formed by winding a plurality of pieces of stranded wire 30 into a multi-line coil form. Thus, the rigidity of the coil body 60 is increased, which improves passing performance of the catheter into a blocked portion or the like.

The smooth outer peripheral surface 63 and the inner peripheral surface 64 (which maintains the outer profile of the stranded wire 30) are formed at the distal end portion 62 of the coil body 60. However, the main body part 61 may also include a smooth outer peripheral surface and an inner peripheral surface (which maintains the outer profile of the stranded wire 30). In this embodiment, it is not necessary to form the distal end portion 62 using a separate part. Thus, the distal end portion 62 may advantageously be integral with the coil body 60.

In some embodiments, the distal end portion 62 is formed by fusing the first wire(s) 31a and the second wire(s) 31b together. Additionally or alternatively, the main body part 61 may be formed of the stranded wire 30, and the distal end portion 62 may be provided separately from the main body part 61. In such a case, the catheter 5 has excellent torque transmissivity and excellent flexibility, improving insertion of the catheter 5 into a blocked portion of a blood vessel. Thus, the catheter 5 may easily restore its original form after being bent or curved.

When the distal end portion 62 is formed by fusing the first wire(s) 31a and the second wire(s) 31b together, it is possible to further improve insertion of the catheter 5 into a blocked portion of a blood vessel. Thus, operability of the catheter 5 with a combination device (such as a guide wire) is improved, and shape restorability of the catheter 5 is superior compared to conventional catheters.

In the disclosed embodiments, the distal end portion 62 may be a fused member such that the first wire(s) 31a and the second wire(s) 31b are welded together. However, the distal end portion 62 may be formed by a method other than welding. For example, the distal end portion 62 may be formed by brazing the first wire(s) 31a and the second wire(s) 31b.

Figure 12:
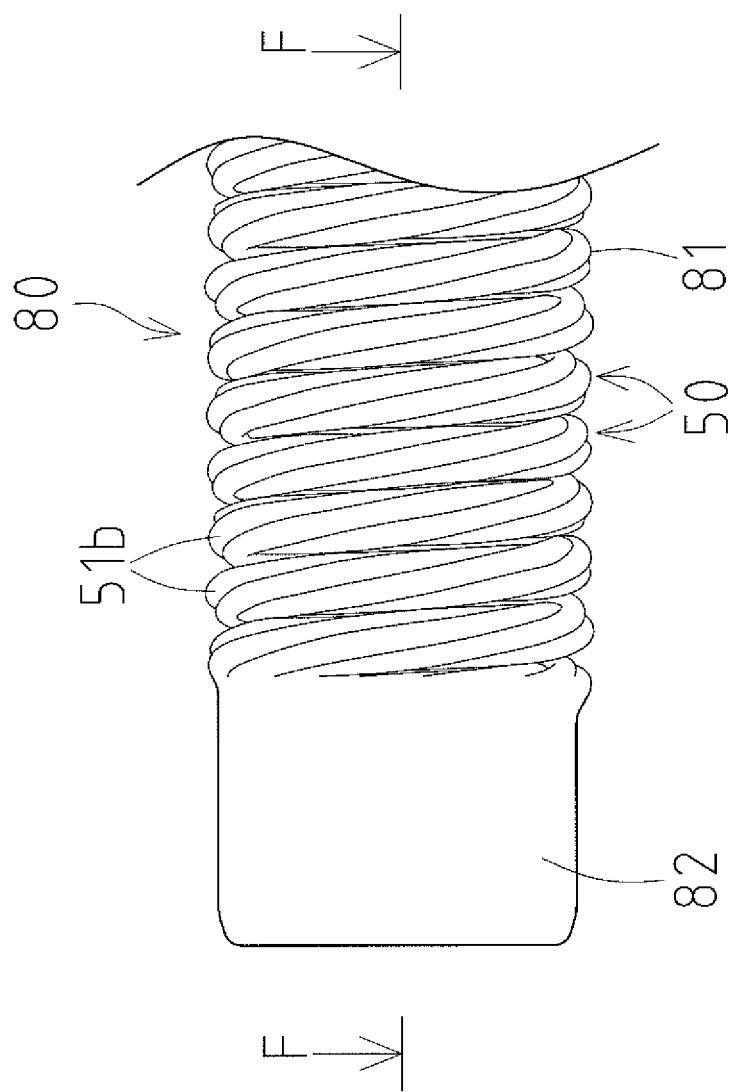
FIG. 12 is a partial enlarged view illustrating a distal end portion of a catheter according to the disclosed embodiments.
Figure 13:
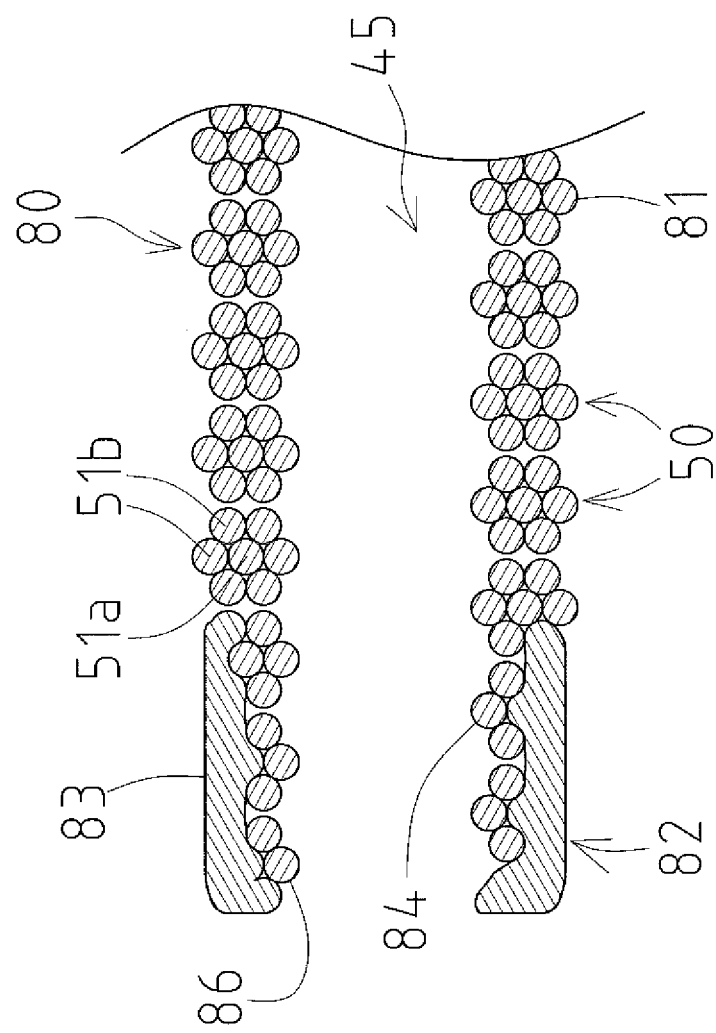
FIG. 13 is a partial section view taken from a line F-F of FIG. 12.

FIG. 12 is a partial enlarged view illustrating a distal end portion of a catheter according to disclosed embodiments. FIG. 13 is a partial section view taken from a line F-F of FIG. 12.

The catheter of FIG. 12 is similar to the catheter 5 except that the catheter of FIG. 12 includes a different number of stranded wires. In FIG. 12, a main body part 81 of a coil body 80 is wound by one bundle of stranded wire 50 in a single coil form. Thus, a single stranded wire 50 is wound to form the coil body 80.

Note that the catheter of FIG. 12 is similar to the catheter of FIGS. 8-11 in that the stranded wire 50 is formed by twisting, for example, six pieces of stainless steel second wire 51b (as side wire) around stainless steel first wire 51a (as a core wire). Additionally, the coil body 80 includes the main body part 81, which extends from the operation part 10 toward the distal end side, and a distal end portion 82, which is positioned distally of the main body part 81. The hollow part 45 is formed in the main body part 81 and in the distal end portion 82. Furthermore, the distal end portion 82 of the coil body 80 is formed so that the distal ends of the stranded wire 50, positioned at the distal end portion 82, are fused and bonded together by, for example, YAG welding, to prevent the first wire(s) 51a and the second wire(s) 51b from coming undone.

As illustrated in FIG. 13, on an outer peripheral surface 83 of the distal end portion 82, the first wire(s) 51a and the second wire(s) 51b, positioned at the distal end portion 82, are fused and bonded together by, for example, YAG welding, so that the first wire(s) 51a and the second wire(s) 51b do not come undone. Additionally, as shown in FIG. 13, the outer peripheral surface 83 at the distal end portion 82 is a smooth surface.

By welding, it is possible to easily fuse only the first wire(s) 51a and the second wire(s) 51b corresponding to the outer peripheral surface 83 without fusing the first wire(s) 51a and the second wire(s) 51b corresponding to the inner peripheral surface 84.

A distal end opening portion 86 at the distal end of the distal end portion 82 is in communication with the hollow part 45, and the stranded wire 50 positioned at the distal end of the distal end portion 82 is fused so as not to come undone.

Also, the outer peripheral surface 83 of the distal end portion 82 is a smooth surface. This reduces resistance when the catheter is inserted into a blocked portion of a blood vessel or the like, thus improving insertion of the catheter into the blocked portion. In contrast to the outer peripheral surface 83, the inner peripheral surface 84 of the distal end portion 82 maintains the outer profile of the stranded wire 50 and, thus, is uneven. This reduces the contact area between the catheter and a combination device, such as a guide wire, that is inserted into the hollow part 45 of the coil body 80. Thus, the inner peripheral surface 84 suppresses sliding resistance and improves operability of the catheter.

Moreover, the distal end portion 82 and the main body part 81 may be integral such that they are formed as a unitary member. This prevents concentration of stress that would cause a break at a border area between the distal end portion 82 and the main body part 81.

The smooth outer peripheral surface 83 and the inner peripheral surface 84 (which maintains the outer profile of the stranded wire 50) are formed at the distal end portion 82 of the coil body 80. However, the main body part 81 may also include a smooth outer peripheral surface and an inner peripheral surface (which maintains the outer profile of the stranded wire 50). In this embodiment, it is not necessary to form the distal end portion 82 using a separate part. Thus, the distal end portion 62 may advantageously be integral with the coil body 80.

Figure 14:
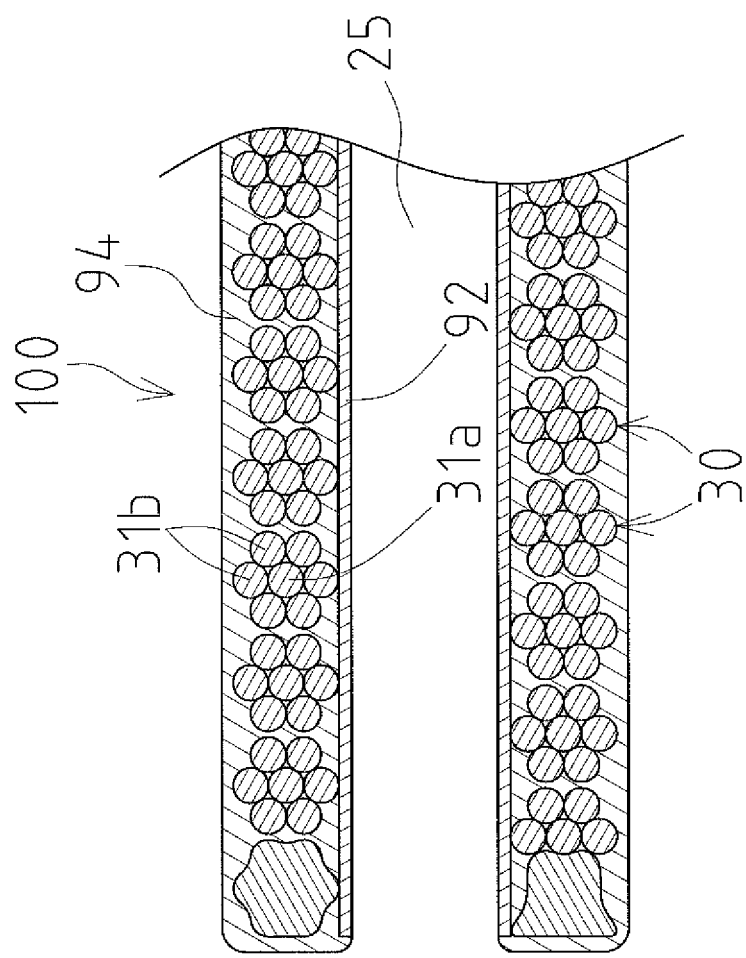
FIG. 14 is a partial section view illustrating a distal end portion of a catheter according to the disclosed embodiments.

FIG. 14 is a partial section view illustrating a distal end portion of a catheter according to disclosed embodiments.

The catheter of FIG. 14 is similar to the catheters 1 and/or 5 except that an outer periphery of the catheter is covered with resin. An inner layer 92 is disposed along the hollow part 25 in a coil body 100. An outer layer 94 is disposed radially outward of the inner layer 92 so as to cover the coil body 100. The outer layer 94 may be formed of resin. In some embodiments, the inner layer 92 may also be formed of resin.

The catheter of FIG. 14 has excellent torque transmissivity and excellent flexibility, thus further improving insertion of the catheter into a blocked portion of a blood vessel. Additionally, operability of the catheter with a combination device, such as a guide wire, is improved compared to conventional catheters.

FIG. 15 is a partial section view illustrating a distal end portion of a catheter according to disclosed embodiments.

The catheter of FIG. 15 is similar to the catheters 1 and/or 5 except that a part of the outer periphery of the catheter is covered with resin. An inner layer 112 is disposed along the hollow part 45 in a coil body 120. An outer layer 114 is disposed radially outward of the inner layer 112 so as to cover the coil body 120. However, as shown in FIG. 15, the outer layer 114 does not cover the coil body along the outer peripheral surface 63. Thus, the outer layer 114 is not disposed over the outer peripheral surface 63. The outer layer 114 may be formed of resin. In some embodiments, the inner layer 112 may also be formed of resin.

The catheter of FIG. 15 has excellent torque transmissivity and excellent flexibility, thus further improving insertion of the catheter into a blocked portion of a blood vessel. Additionally, operability of the catheter with a combination device such as a guide wire is improved compared to conventional catheters.

The present disclosure shall not be limited to the embodiments provided above, and modifications in design can appropriately be made. Additionally, the embodiments provided above may be combined and intermixed.

What is claimed is:

1. A catheter, comprising:
   at least one twisted wire bundle comprising a plurality of wires wound about a first helical axis, the twisted wire bundle being helically wound about a second helical axis, different from the first helical axis, to form a hollow coil body around a central lumen of the catheter,
   wherein:
      a distal end portion of the hollow coil body includes an outer peripheral surface and an inner peripheral surface,
      the plurality of wires at the distal end portion of the hollow coil body are welded together at the outer peripheral surface, and the plurality of wires at the distal end portion of the hollow coil body are not welded together at the inner peripheral surface,
      the inner peripheral surface maintains an outer profile of the twisted wire bundle at the distal end portion, and
      the twisted wire bundle extends to the distal-most end of the catheter.

2. The catheter according to claim 1, further comprising an inner layer and an outer layer, the outer layer being disposed radially outward of the inner layer so as to cover the hollow coil body.

3. The catheter according to claim 1, wherein the at least one twisted wire bundle is a single twisted wire bundle.

4. The catheter according to claim 1, wherein the twisted wire bundle further comprises a center core wire, and the plurality of wires are wound about the center core wire.

5. The catheter according to claim 1, wherein at least one of the plurality of wires at the inner peripheral surface is in direct contact with at least one of the plurality of wires at the outer peripheral surface.

6. The catheter according to claim 1, wherein:
   the outer peripheral surface is a smooth surface,
   the inner peripheral surface is an uneven surface, and
   at least one of the plurality of wires at the uneven inner peripheral surface is in direct contact with at least one of the plurality of wires at the smooth outer peripheral surface.

7. The catheter according to claim 1, wherein the plurality of wires at the distal end portion of the hollow coil body defines a distal end opening at the distal-most end of the catheter.

8. The catheter according to claim 1, wherein the outer peripheral surface is a continuous even surface.

9. The catheter according to claim 8, wherein the inner peripheral surface is an uneven surface.

10. The catheter according to claim 1, comprising a plurality of the twisted wire bundles helically wound about the second helical axis.

11. The catheter according to claim 10, further comprising an inner layer and an outer layer, the outer layer being disposed radially outward of the inner layer so as to cover the hollow coil body.

12. The catheter according to claim 10, wherein the plurality of wires extend in a direction substantially parallel to a longitudinal axis of the catheter.

* * * * *